(12) United States Patent
Rezach

(10) Patent No.: US 10,888,357 B2
(45) Date of Patent: Jan. 12, 2021

(54) SPINAL IMPLANT SYSTEM AND METHOD

(71) Applicant: Warsaw Orthopedic, Inc., Warsaw, IN (US)

(72) Inventor: William Alan Rezach, Atoka, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 275 days.

(21) Appl. No.: 15/056,762

(22) Filed: Feb. 29, 2016

(65) Prior Publication Data
US 2017/0245900 A1   Aug. 31, 2017

(51) Int. Cl.
*A61B 17/70* (2006.01)

(52) U.S. Cl.
CPC ...... *A61B 17/7055* (2013.01); *A61B 17/7035* (2013.01); *A61B 17/7037* (2013.01); *A61B 17/7041* (2013.01)

(58) Field of Classification Search
CPC combination set(s) only.
See application file for complete search history.

(56) References Cited

U.S. PATENT DOCUMENTS

| | | | |
|---|---|---|---|
| 5,330,473 A | 7/1994 | Howland | |
| 5,580,184 A | 12/1996 | Riccitelli | |
| 5,720,746 A | 2/1998 | Soubeiran | |
| 6,063,090 A * | 5/2000 | Schlapfer | A61B 17/7037 606/270 |
| 6,796,984 B2 | 9/2004 | Soubeiran | |
| 7,955,357 B2 | 6/2011 | Kiester et al. | |
| 7,981,025 B2 | 7/2011 | Pool et al. | |
| 8,057,472 B2 | 11/2011 | Walker et al. | |
| 8,137,349 B2 | 3/2012 | Soubeiran | |
| 8,197,490 B2 | 6/2012 | Pool et al. | |
| 8,262,702 B2 * | 9/2012 | Giger | A61B 17/7035 606/246 |
| 8,343,192 B2 | 1/2013 | Kiester | |
| 8,382,756 B2 | 2/2013 | Pool et al. | |
| 8,419,734 B2 | 4/2013 | Walker et al. | |
| 8,632,548 B2 | 1/2014 | Soubeiran | |
| 9,055,980 B2 * | 6/2015 | Biedermann | A61B 17/7041 |
| 10,070,895 B2 * | 9/2018 | Barra | A61B 17/7074 |
| 2004/0111088 A1 * | 6/2004 | Picetti | A61B 17/7001 606/265 |
| 2004/0169281 A1 | 9/2004 | Nguyen et al. | |
| 2005/0246034 A1 | 11/2005 | Soubeiran | |
| 2005/0251109 A1 | 11/2005 | Soubeiran | |
| 2005/0267472 A1 * | 12/2005 | Biedermann | A61B 17/7032 606/308 |
| 2006/0200131 A1 * | 9/2006 | Chao | A61B 17/7037 606/278 |
| 2006/0235392 A1 * | 10/2006 | Hammer | A61B 17/7034 606/264 |

(Continued)

*Primary Examiner* — Jan Christopher L Merene
(74) *Attorney, Agent, or Firm* — Sorell, Lenna & Schmidt, LLP

(57) ABSTRACT

A spinal construct includes a fastener configured for attachment with sacral and/or pelvic tissue of a body. A connector includes a mating element engageable with the fastener and includes a receiver. A spinal implant is engageable with the receiver between a capture configuration and a removable configuration. A multi-axial fastener is connected with the spinal implant. Systems, implants, instruments and methods of use are disclosed.

20 Claims, 7 Drawing Sheets

(56) References Cited

U.S. PATENT DOCUMENTS

| | | | |
|---|---|---|---|
| 2006/0282074 A1* | 12/2006 | Renaud | A61B 17/7035 606/279 |
| 2007/0233087 A1* | 10/2007 | Schlapfer | A61B 17/7035 606/86 A |
| 2008/0021454 A1* | 1/2008 | Chao | A61B 17/7044 606/250 |
| 2008/0154306 A1* | 6/2008 | Heinz | A61B 17/7055 606/256 |
| 2008/0195159 A1* | 8/2008 | Kloss | A61B 17/704 606/305 |
| 2008/0269810 A1* | 10/2008 | Zhang | A61B 17/7001 606/305 |
| 2008/0294203 A1* | 11/2008 | Kovach | A61B 17/7032 606/308 |
| 2009/0036929 A1* | 2/2009 | Reglos | A61B 17/7035 606/278 |
| 2009/0062915 A1 | 3/2009 | Kohm et al. | |
| 2009/0112262 A1 | 4/2009 | Pool et al. | |
| 2009/0131983 A1* | 5/2009 | Biedermann | A61B 17/7032 606/246 |
| 2009/0287252 A1 | 11/2009 | Marik et al. | |
| 2010/0036433 A1* | 2/2010 | Jackson | A61B 17/7037 606/302 |
| 2011/0034957 A1* | 2/2011 | Biedermann | A61B 17/7035 606/305 |
| 2011/0238126 A1 | 9/2011 | Soubeiran | |
| 2011/0270314 A1* | 11/2011 | Mueller | A61B 17/704 606/264 |
| 2012/0179205 A1* | 7/2012 | Miller | A61B 17/7041 606/264 |
| 2012/0179215 A1 | 7/2012 | Soubeiran | |
| 2012/0221053 A1* | 8/2012 | Copf | A61B 17/7032 606/251 |
| 2012/0226316 A1* | 9/2012 | Dant | A61B 17/7007 606/250 |
| 2012/0253398 A1* | 10/2012 | Metcalf | A61B 17/7037 606/264 |
| 2012/0259367 A1 | 10/2012 | Lange | |
| 2013/0085534 A1* | 4/2013 | Hainard | A61B 17/7055 606/278 |
| 2013/0304128 A1* | 11/2013 | Lange | A61B 17/705 606/264 |
| 2014/0018858 A1* | 1/2014 | Laeng | A61B 17/7002 606/270 |
| 2015/0057708 A1* | 2/2015 | Ballard | A61B 17/7041 606/278 |
| 2015/0359568 A1* | 12/2015 | Rezach | A61B 17/7032 606/266 |
| 2017/0027615 A1* | 2/2017 | Rezach | A61B 17/7032 |
| 2017/0086895 A1* | 3/2017 | Barra | A61B 17/8605 |

* cited by examiner

US 10,888,357 B2

SPINAL IMPLANT SYSTEM AND METHOD

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and plates can be used to provide stability to a treated region. For example, during surgical treatment, surgical instruments can be used to deliver components of the spinal constructs to the surgical site for fixation with bone to immobilize a joint. Fasteners may also be attached to iliac bone. This disclosure describes an improvement over these prior technologies.

SUMMARY

In one embodiment, a spinal construct is provided. The spinal construct includes a fastener configured for attachment with sacral and/or pelvic tissue of a body. A connector includes a mating element engageable with the fastener and includes a receiver. A spinal implant is engageable with the receiver between a capture configuration and a removable configuration. A multi-axial fastener is connected with the spinal implant. Systems, implants, instruments and methods of use are disclosed.

In one embodiment, a method for treating a spine is provided. The method comprises the steps of: engaging a fastener of a spinal construct with an ala of a sacrum; engaging a multi-axial fastener of the spinal construct with an S1 vertebra of the sacrum; connecting a spinal rod of the spinal construct with a receiver of a connector of the spinal construct; engaging a coupling member with the spinal rod to fix the spinal rod with the receiver; connecting the spinal rod with the multi-axial fastener; engaging the connector with the fastener, and removing the spinal rod from the receiver to selectively adjust the spinal construct.

BRIEF DESCRIPTION OF THE DRAWINGS

The present disclosure will become more readily apparent from the specific description accompanied by the following drawings, in which.

DETAILED DESCRIPTION

Figure 1:
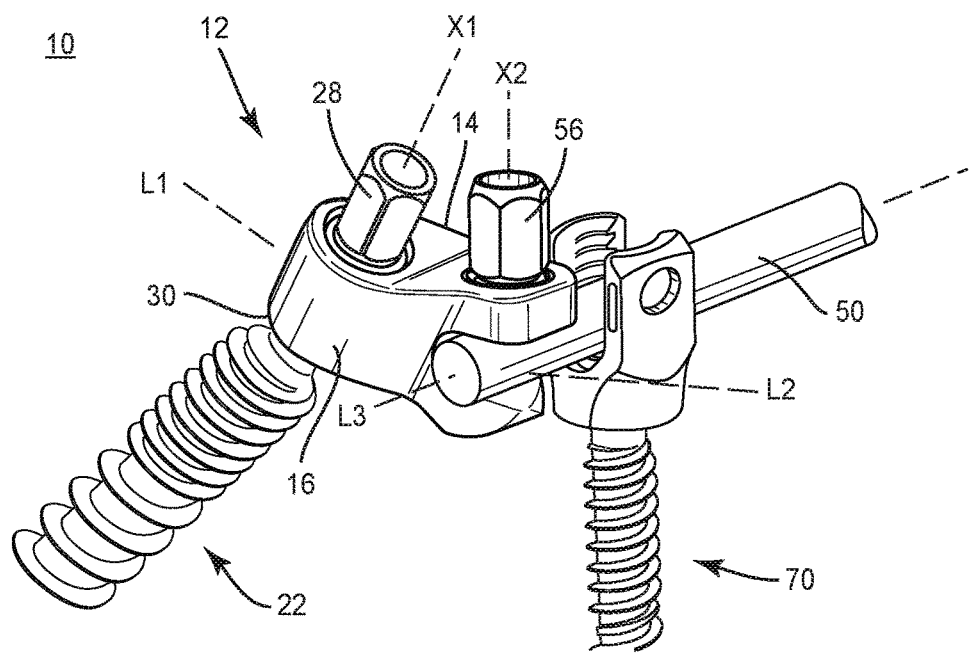
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In some embodiments, the systems and methods of the present disclosure are employed with a spinal joint and fusion, for example, with a cervical, thoracic, lumbar and/or sacral region of a spine.

In some embodiments, the system of the present disclosure comprises a spinal construct having one or more implants, such as, for example, a connector having an S2-alar-iliac (S2AI) fixation receiver. In some embodiments, the connector includes a low profile receiver for S2AI screw placement. In some embodiments, the connector includes a receiver that has a built in connector to position onto rod. In some embodiments, the connector includes a device that allows easy revision of an iliac screw. In some embodiments, the connector includes a receiver that is biased such that iliac screw angulation can meet trajectory requirements.

In some embodiments, the system comprises a spinal construct having one or more implants, such as, for example, a S2AI connector. In some embodiments, the connector includes a low profile receiver for S2AI fixation. In some embodiments, the connector includes a receiver to position onto a spinal rod. In some embodiments, the connector facilitates iliac screw revision. In some embodiments, the connector includes a receiver biased such that screw angulation can meet trajectory requirements.

In some embodiments, the system comprises a spinal construct having one or more implants, such as, for example, a connector including a receiver that attaches onto spinal rod and a S2AI screw. In some embodiments, the receiver includes a side or lateral loading cavity for receiving the spinal rod. In some embodiments, the spinal construct includes a S1 multi-axial screw. In some embodiments, the spinal construct includes staggered setscrews to allow for surgical instrument attachment. In some embodiments, the system provides a reduced profile spinal construct disposed about a spinal rod. In some embodiments, the system facilitates positioning a spinal construct along a sacrum anatomy.

In some embodiments, the system is utilized with a method including the step of implanting an iliac screw with an alar of a sacrum. In some embodiments, the method includes the step of implanting a multi-axial bone screw with the sacrum. In some embodiments, the method includes the step of assembling a spinal rod with a receiver of a connector. In some embodiments, the method includes the step of bending the spinal rod. In some embodiments, the method includes the step of connecting the spinal rod with the multi-axial screw. In some embodiments, the method includes the step of connecting the connector with the iliac screw. In some embodiments, the method includes the step of engaging break-off setscrews with the connector to fix the spinal rod and the iliac screw with the connector. In some embodiments, the method includes the step of removing setscrews and rotating the connector off of the spinal rod to revise positioning of the iliac screw. In some embodiments, the method includes the step of backing out the iliac screw from tissue.

In some embodiments, the present system and/or method is used with surgical navigation, such as, for example, fluoroscope or image guidance. In some embodiments, the presently disclosed system and/or method reduce operating time for a surgical procedure and reduce radiation exposure due to fluoroscope or image guidance, for example, by eliminating procedural steps and patient repositioning by implanting system components in one body position.

In one embodiment, one or all of the components of the system are disposable, peel-pack or pre-packed sterile devices. One or all of the components of the system may be reusable. The system may be configured as a kit with multiple sized and configured components.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, muscle, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-10, there are illustrated components of a spinal implant system 10, in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as poly-aetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal construct 12. Spinal construct 12 includes a connector 14. In some embodiments, connector 14 is configured for disposal in a medial-lateral orientation between a sacrum and a sacral ala. Connector 14 includes a body 16. Body 16 defines a transverse axis L1. In some embodiments, body 16 can be variously configured, such as, for example, oval, oblong, triangular, square, polygonal, irregular, uniform, non-uniform, variable, hollow and/or tapered. Body 16 includes a low profile configuration to facilitate insertion and manipulation of connector 14, as described herein. Body 16 includes a surface 18 that defines a cavity, such as, for example, an opening 20. Opening 20 defines an axis X1.

In some embodiments, opening 20 is oriented to implant a fastener, such as, for example, an alar iliac screw 22, as described herein with tissue, such as, for example, an ala of a sacrum and/or iliac bone. Opening 20 is configured to implant alar screw 22 along axis X1. In some embodiments, opening 20 is aligned with a surgical pathway, approach and/or trajectory, as described herein, to orient alar screw 22 for implantation with an alar region of a sacrum. In some embodiments, opening 20 is aligned with a surgical pathway, approach and/or trajectory that communicates with a posterior mid-line surgical pathway, approach and/or trajectory, as described herein.

Surface 18 includes an engagement surface 24 that defines a mating element (not shown). In some embodiments, the mating element defines a particularly configured engagement surface configured to interface in a selective mating engagement with a head 62 of alar screw 22, as described herein. The mating element is configured to capture head 62 of alar screw 22. In some embodiments, the mating element can include arcuate surfaces and planar surfaces configured to interface with head 62 of alar screw 22 in a keyed connection. In some embodiments, the mating element is configured to resist and/or prevent rotation of alar screw 22 about a selected axis. In some embodiments, engagement surface 24 includes flats and/or arcuate surfaces to form various bone screw configurations, such as, for example, multi-axial screws, sagittal angulation screws, pedicle screws, mono-axial screws, uni-planar screws, fixed screws, anchors, tissue penetrating screws, conventional screws, expanding screws. In some embodiments, head 62 is slidably engageable with engagement surface 24 such that alar screw 22 is rotatable along a plurality of axes relative to connector 14 including rotation about axis X1. In some embodiments, engagement surface 24 is configured for disposal of a ring (not shown). In some embodiments, the ring is expandable and resilient between a contracted and/or capture orientation and an expanded orientation to facilitate engagement of alar screw 22 with connector 14.

In some embodiments, surface 18 includes a surface 26. Surface 26 includes a thread form configured for engagement with a coupling member, such as, for example, a setscrew 28. Setscrew 28 is configured for removal and re-engagement such that alar screw 22 is selectively adjustable, for example, during revision of positioning of one or more components of spinal construct 12 and/or a surgical procedure employing spinal construct 12, as described herein. In some embodiments, setscrew 28 includes an end having a hexagonal geometry configured for engagement with a similarly shaped surgical tool, such as, for example, a driver. In some embodiments, setscrew 28 includes an end having a cruciform, phillips, square, hexalobe, polygonal or star cross sectional configuration for disposal of a correspondingly shaped portion of a driver. Setscrew 28 is configured to fix and/or lock alar screw 22 either provisionally or permanently with tissue of the ala, as described herein.

In some embodiments, setscrew 28 includes at least two portions connected at a reduced diameter section forming a frangible connection and a break-off portion. In some embodiments, the portions are fabricated from a fracturing and/or frangible material such that manipulation of one portion relative to the second portion can fracture and separate the portions at a predetermined force and/or torque limit, as described herein. In some embodiments, as force and/or torque is applied and resistance increases, for example, due to fixation of a portion with surface 26, as described herein, the predetermined torque and force limit is approached. In some embodiments, the portions include offset hex geometries.

In some embodiments, the portions can fracture and separate at a predetermined force or torque limit, which may be in a range of approximately 6.7 Newton meters (N-cm) to 12 N-m. In some embodiments, the portions may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of the portions.

Body 16 includes a surface 30. In some embodiments, surface 30 may be spaced apart from tissue of the ala upon implantation of spinal construct 12. In some embodiments, surface 30 may engage tissue of the ala upon implantation of spinal construct 12. In some embodiments, surface 30 may include alternate surface configurations, such as, for example, rough, arcuate, undulating, mesh, porous, semi-porous, dimpled and/or textured.

Figure 10:
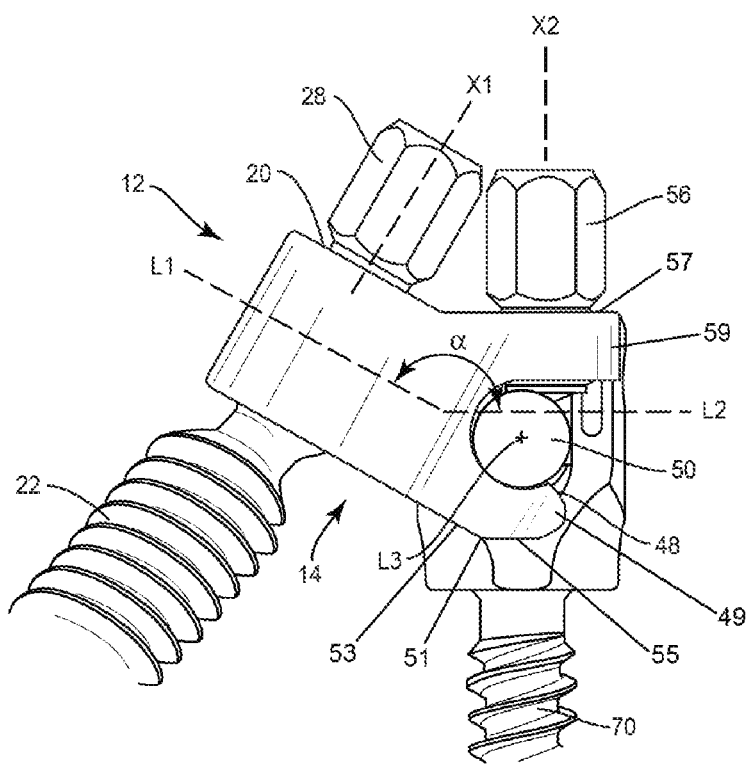
FIG. 10 is a side view of components of one embodiment of a system in accordance with the principles of the present disclosure.

Connector 14 includes a wall 40 having an inner surface 42. Wall 40 includes extensions 44, 46 that extend along surface 42 to define a lateral and/or side loading implant cavity. Extensions 44, 46 define a receiver 48, which includes the implant cavity configured for disposal of a spinal implant. Receiver 48 defines a transverse axis L2 and is configured for disposal of a spinal implant, such as, for example, a spinal rod 50. In some embodiments, axis L2 is disposed at an angle α relative to axis L1, as shown in FIG. 10. In some embodiments, angle α includes a range of 0 through 270 degrees. In some embodiments, angle α is approximately 135 degrees.

Figure 7:
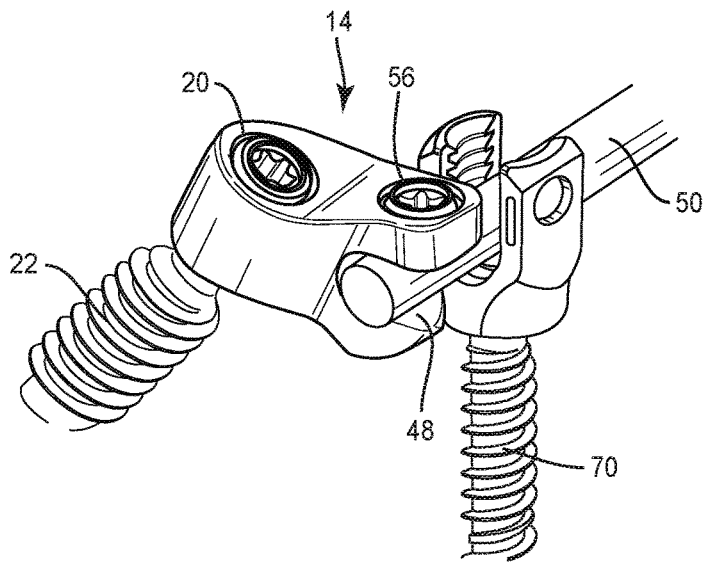
FIG. 7 is a perspective view of the components shown in FIG. 6.
Figure 8:
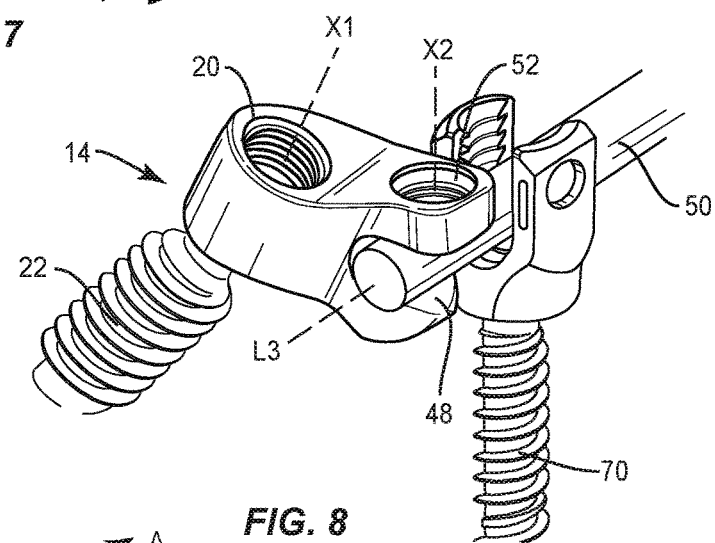
FIG. 8 is a perspective view of components of one embodiment of a system in accordance with the principles of the present disclosure.
Figure 9:
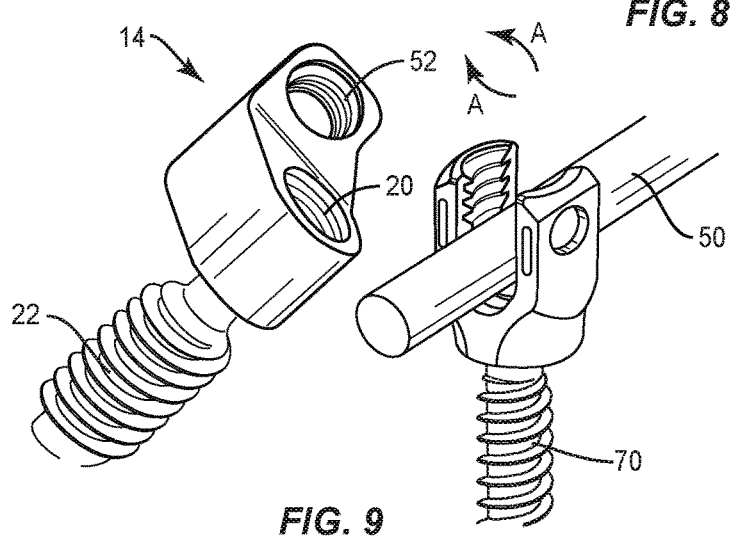
FIG. 9 is a perspective view of the components shown in FIG. 8 with parts separated.

Receiver 48 defines a longitudinal axis L3. Axis L3 is disposed transverse relative to axis L2 and axis X1. In some embodiments, axis L3 may be disposed in various orientations, such as, for example, perpendicular, transverse and/or at angular orientations, such as acute or obtuse relative to axis L2 and/or axis X1. Spinal rod 50 is configured for disposal between a capture configuration within receiver 48, as shown in FIG. 7, and a removable configuration such that spinal rod 50 is rotatably removable from receiver 48, as shown in FIGS. 8 and 9, as described herein. In some embodiments, spinal rod 50 is selectively adjustable relative to connector 14, for example, during a revision case or the repositioning of one or more components of spinal construct 12 and/or a surgical procedure employing spinal construct 12, as described herein. In some embodiments, spinal rod 50 is configured for connection with a fastener, such as, for example, a multi-axial fastener (MAS) 70, as described herein.

In some embodiments, receiver 48 may have various cross section configurations, such as, for example, oval, oblong, triangular, rectangular, square, polygonal, irregular, uniform, non-uniform, variable and/or tapered. In some embodiments, surface 42 may include gripping elements or surfaces, such as, for example, rough, arcuate, undulating, mesh, porous, semi-porous, dimpled and/or textured to facilitate engagement with spinal rod 50. In some embodiments, extensions 44, 46 provide a minimal profile about spinal rod 50 to facilitate placement with the sacrum, as described herein.

Figure 11:
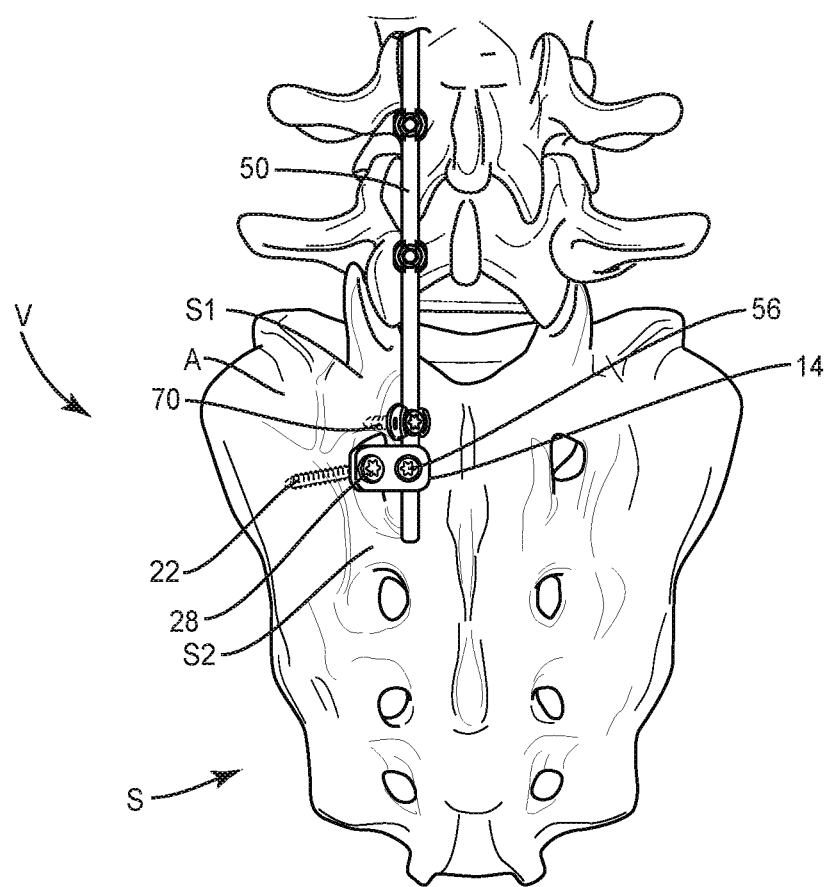
FIG. 11 is a plan view of components of one embodiment of a system in accordance with the principles of the present disclosure disposed with vertebrae.
Figure 12:
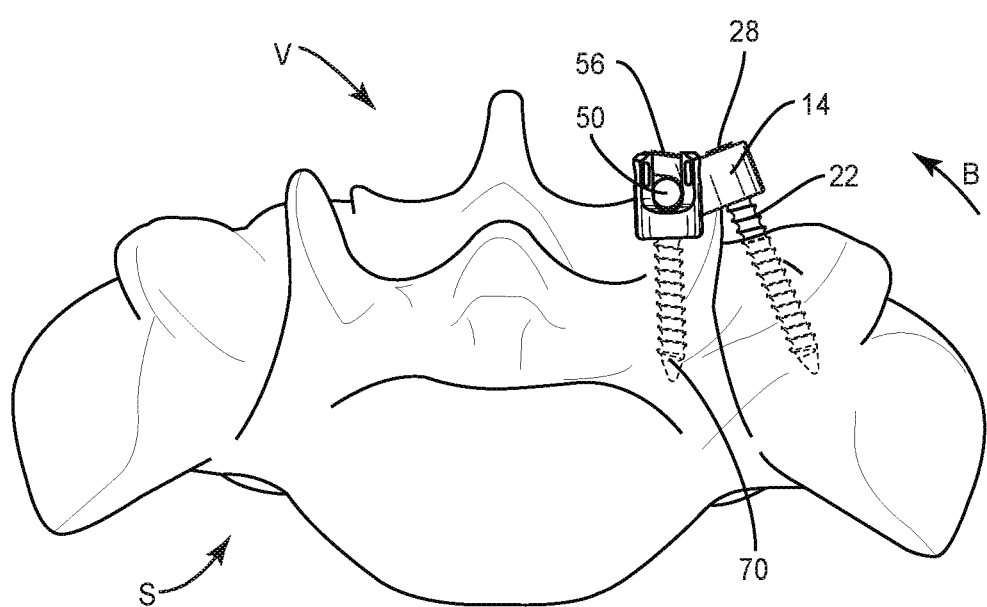
FIG. 12 is an axial view of components of one embodiment of a system in accordance with the principles of the present disclosure disposed with vertebrae.

Receiver 48 includes a surface 52 that defines a cavity, such as, for example, an opening 54. Opening 54 is disposed in communication with receiver 48 for disposal of a coupling member, as described herein, to connect spinal rod 50 with connector 14. Opening 54 defines an axis X2. In some embodiments, opening 54 is disposed separate and apart from opening 20 along the surface of connector 14. In some embodiments, as shown in FIG. 8, axis X2 is disposed offset and/or staggered from axis X1 such that a surgical instrument is engageable with connector 14 for selective adjustment, for example, during a revision case or repositioning of one or more components of spinal construct 12 and/or a surgical procedure employing spinal construct 12, as described herein. In some embodiments, as shown in FIGS. 11 and 12, axis X2 is disposed offset and/or staggered from axis X1 in a coronal plane of vertebrae V, as described herein, such that a surgical instrument is engageable with connector 14 for selective adjustment, for example, during a revision case or repositioning of one or more components of spinal construct 12 and/or a surgical procedure employing spinal construct 12, as described herein. In some embodiments, axis X2 is disposed transverse to axis X1. In some embodiments, axis X2 may be disposed in various orientations, such as, for example, perpendicular, transverse and/or at angular orientations, such as acute or obtuse relative to axis X1. In some embodiments, receiver 48 includes an arm 49. Arm 49 includes an outer surface 51. Outer surface 51 of arm 49 includes a section 53 and a section 55. Section 55 extends substantially parallel to an outer surface 57 of another arm 59 of receiver 48, as shown in FIG. 10, for example. In some embodiments, surface 57 extends at an acute angle relative to section 53, and vice versa.

Surface 52 is threaded and configured for disposal of a coupling member, such as, for example, a setscrew 56. Setscrew 56 is disposable between a non-locking orientation, such that spinal rod 50 is translatable relative to receiver 48 and a locked orientation, such that setscrew 56 fixes spinal rod 50 with receiver 48. Setscrew 56 is configured for removal and re-engagement such that spinal rod 50 is selectively adjustable, for example, during revision of positioning of one or more components of spinal construct 12 and/or a surgical procedure employing spinal construct 12, as described herein. In some embodiments, spinal rod 50 extends along one or a plurality of vertebra, as described herein. In some embodiments, spinal implant system 10 may include one or a plurality of spinal rods 50, which may be relatively disposed in a side by side, irregular, uniform, non-uniform, offset and/or staggered orientation or arrangement.

In some embodiments, setscrew 56 includes an end having a hexagonal geometry configured for engagement with a similarly shaped surgical tool, such as, for example, a driver. In some embodiments, setscrew 56 includes an end having a cruciform, phillips, square, hexalobe, polygonal or star cross sectional configuration for disposal of a correspondingly shaped portion of a driver. Setscrew 56 is configured for engagement with spinal rod 50 to facilitate fixation and/or locking of spinal rod 50 with connector 14 in a capture configuration.

In some embodiments, setscrew 56 includes at least two portions connected at a reduced diameter section forming a frangible connection and a break-off portion. In some embodiments, the portions are fabricated from a fracturing and/or frangible material such that manipulation of one portion relative to the second portion can fracture and separate the portions at a predetermined force and/or torque limit, as described herein. In some embodiments, as force and/or torque is applied and resistance increases, for example, due to fixation of a portion with opening 54, as described herein, the predetermined torque and force limit is approached. In some embodiments, the portions include offset hex geometries.

In some embodiments, the portions can fracture and separate at a predetermined force or torque limit, which may be in a range of approximately 6.7 N-m to 12 N-m. In some embodiments, the portions may have the same or alternate cross section configurations, may be fabricated from a homogenous material or heterogeneously fabricated from different materials, and/or alternately formed of a material having a greater degree, characteristic or attribute of plastic deformability, frangible property and/or break away quality to facilitate fracture and separation of the portions.

Spinal implant system 10 includes alar screw 22. Alar screw 22 is configured for insertion into an ala region of a sacrum, as described herein. Alar screw 22 includes shaft 60 having a substantially cylindrical cross-section along its length and head 62. Shaft 60 includes an outer surface having an external thread form. In some embodiments, the external thread form may include a single thread turn or a plurality of discrete threads. Head 62 includes a tool engaging portion 64 configured to engage a surgical tool or instrument, as described herein. In one embodiment, portion 64 includes a hexagonal cross-section to facilitate engagement with a surgical tool or instrument, as described herein. In some embodiments, portion 64 may have alternative cross-sections, such as, for example, rectangular, polygonal, hexalobe, oval, or irregular.

Figure 2:
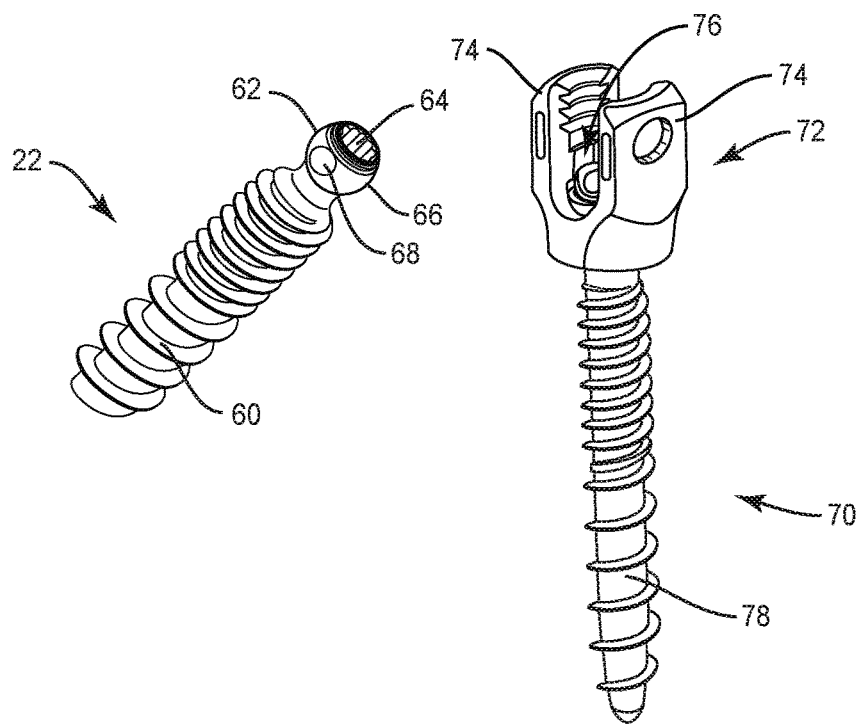
FIG. 2 is a perspective view of components of one embodiment of a system in accordance with the principles of the present disclosure.
Figure 3:
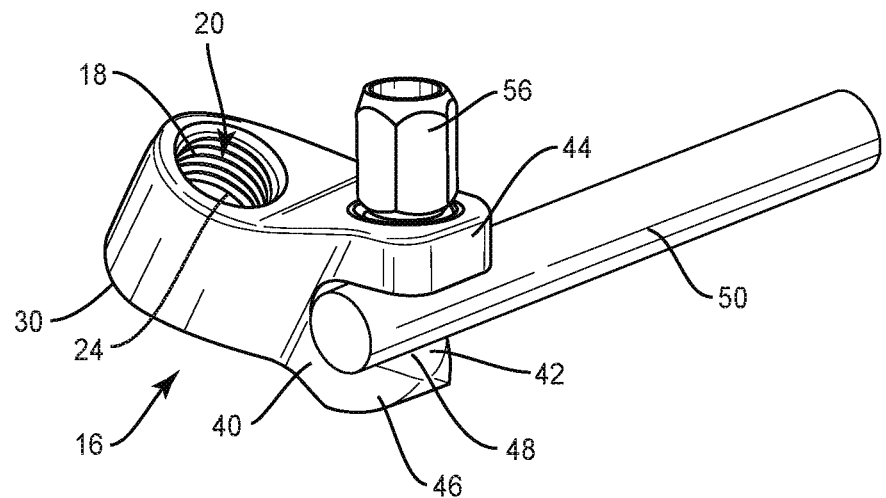
FIG. 3 is a perspective view of components of one embodiment of a system in accordance with the principles of the present disclosure.
Figure 4:
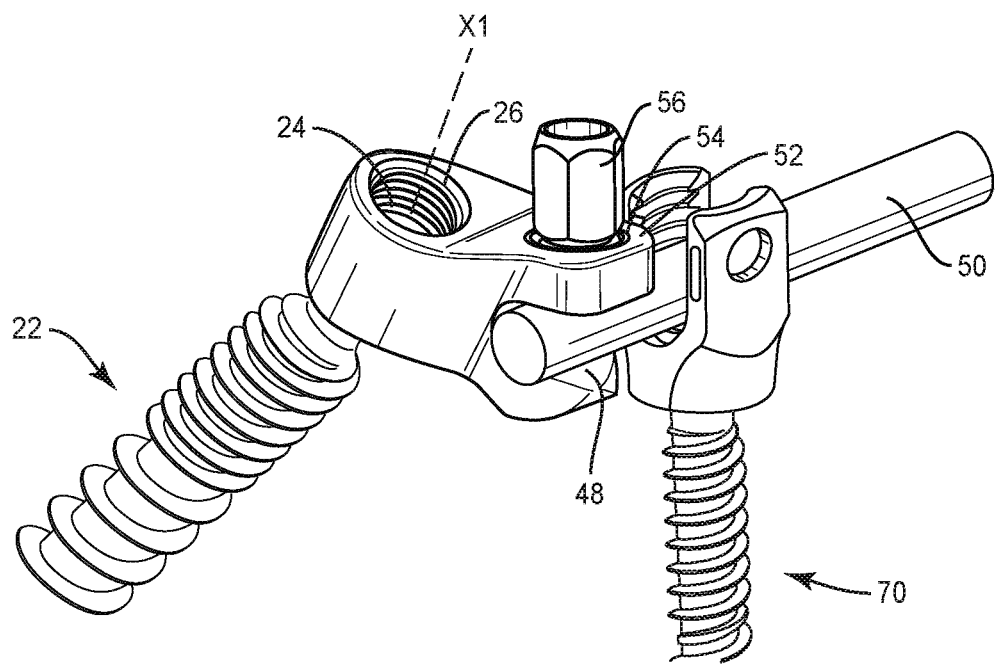
FIG. 4 is a perspective view of a component of one embodiment of a system in accordance with the principles of the present disclosure.
Figure 5:
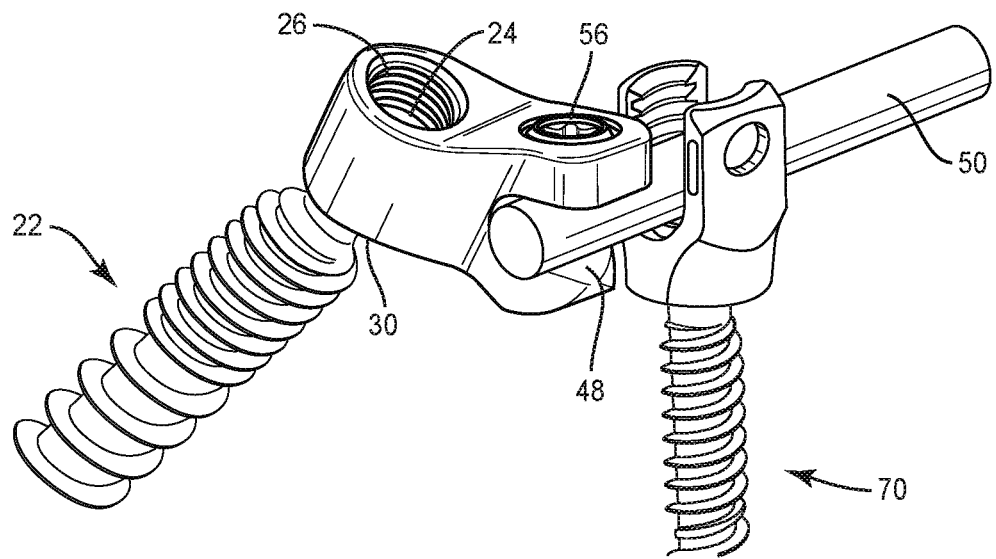
FIG. 5 is a perspective view of components of one embodiment of a system in accordance with the principles of the present disclosure.
Figure 6:
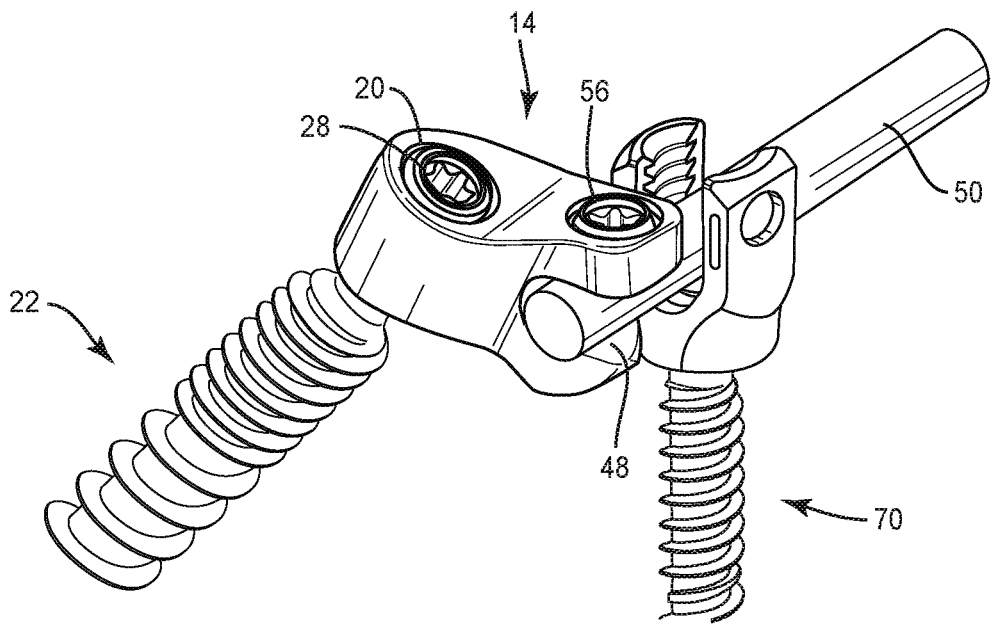
FIG. 6 is a perspective view of components of one embodiment of a system in accordance with the principles of the present disclosure.

In some embodiments, as shown in FIG. 2, head 62 includes a mating surface, such as, for example, arcuate surfaces 66 and planar surfaces 68 configured to mate with the mating element of engagement surface 24, as described herein. In some embodiments, head 62 is slidably engageable with engagement surface 24 in a keyed connection such that shaft 60 is rotatable along a single axis and/or within a single plane relative to connector 14. In some embodiments, alar screw 22 is configured for a snap fit and/or pop fit with engagement surface 24 to facilitate engagement with connector 14. In some embodiments, alar screw 22 has varied lengths, such as, for example, 30 millimeters (mm), 35 mm, 40 mm, 45 mm or 50 mm and/or spinal implant system 10 can comprise a kit with such variously sized alar screws 22.

Spinal implant system 10 includes MAS 70. MAS 70 is configured for implantation with tissue, such as, for example, a vertebra of a sacrum, as described herein. MAS 70 includes a head 72 having a pair of spaced apart arms 74. Arms 74 include an inner surface that defines a U-shaped passageway 76, as shown in FIG. 2. Passageway 76 is configured for disposal of spinal rod 50. In some embodiments, all or only a portion of passageway 76 may have alternate cross section configurations, such as, for example, oval, oblong, triangular, square, polygonal, irregular, uniform, non-uniform, offset, staggered, and/or tapered. In some embodiments, arms 74 may be disposed at alternate orientations, relative to a longitudinal axis of MAS 70, such as, for example, transverse, perpendicular and/or other angular orientations such as acute or obtuse, co-axial and/or may be offset or staggered. The inner surface of head 72 includes a thread form configured for engagement with a coupling member, such as, for example, a setscrew (not shown), similar to those described herein. The setscrew is threaded with head 72 to attach, fix and/or lock spinal rod 50, either provisionally or permanently, with MAS 70, as described herein.

MAS 70 includes a shaft 78 configured for penetrating tissue, such as, for example, a sacrum. Shaft 78 has a cylindrical cross-sectional configuration and includes an outer surface having an external thread form. In some embodiments, the external thread form may include a single thread turn or a plurality of discrete threads. In some embodiments, other engaging structures may be located on shaft 78, such as, for example, a nail configuration, barbs, expanding elements, raised elements and/or spikes to facilitate engagement of shaft 78 with tissue.

In some embodiments, all or only a portion of shaft 78 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 78 may include one or a plurality of openings. In some embodiments, all or only a portion of the outer surface of shaft 78 may have alternate surface configurations to enhance fixation with tissue, such as, for example, rough, arcuate, undulating, mesh, porous, semi-porous, dimpled and/or textured. In some embodiments, all or only a portion of shaft 78 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 78 may be cannulated.

In assembly, operation and use, spinal implant system 10, similar to the systems and methods described herein, is employed with a surgical procedure for treatment of a spinal disorder affecting a section of a spine of a patient, as discussed herein. Spinal implant system 10 is employed with a surgical procedure for treatment of a condition or injury of an affected section of the spine including vertebrae V, as shown in FIGS. 11 and 12, to connect spinal construct 12 with vertebrae V and/or iliac bone. In some embodiments, the components of spinal implant system 10 are attached to vertebrae V including a sacrum S.

In use, to treat a selected section of vertebrae V and/or iliac bone, a medical practitioner obtains access to a surgical site including vertebrae V in any appropriate manner, such as through incision and retraction of tissues. In some embodiments, spinal implant system 10 can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of spinal implant system 10. A preparation instrument (not shown) can be employed to prepare tissue surfaces of vertebrae V, as well as for aspiration and irrigation of a surgical region.

In some embodiments, spinal implant system 10 comprises a kit including a plurality of alar screws 22 of varying configuration and/or dimension, as described herein. In some embodiments, alar screw 22 is selected from the kit for employing with the treatment at the surgical site. Alar screw 22 is delivered along a surgical pathway to the surgical site. A surgical driver is connected with alar screw 22 to align, penetrate and fasten alar screw 22 with an ala region A of sacrum S and/or iliac bone.

MAS 70 is delivered along the surgical pathway to the surgical site. A surgical driver is connected with MAS 70 to align, penetrate and fasten MAS 70 with tissue of sacrum S in an S1 vertebra. Spinal rod 50 is assembled with connector 14 by laterally loading spinal rod 50 with the laterally receiving implant cavity of receiver 48 between extensions 44, 46. Spinal rod 50 is manipulated within receiver 48 for positioning relative to connector 14. In some embodiments, spinal rod 50 may be manipulated and/or deformed, for example, via bending to a selected configuration.

A surgical driver is connected with setscrew 56 and setscrew 56 is disposed with opening 54 and engaged with surface 52 to provisionally fix or permanently fix spinal rod 50 in a capture configuration with receiver 48 and/or in a selected orientation with tissue. In some embodiments, assembled connector 14/spinal rod 50 are delivered along the surgical pathway to the surgical site to connect spinal rod 50 with the components of spinal construct 12, for example, alar screw 22 and MAS 70. In some embodiments, connector 14 and spinal rod 50 are delivered separately to the surgical site.

Receiver 48 includes a minimal profile about spinal rod 50 to facilitate positioning of connector 14 along sacrum S and with the components of spinal construct 12. In some embodiments, receiver 48 includes a perimeter and/or defines a profile that is sized for alignment with a perimeter and/or a profile of head 72 of MAS 70, as shown in FIG. 10. In some embodiments, the perimeter and/or profile of receiver 48 is aligned within and is smaller in dimension than the perimeter and/or profile of head 72.

Spinal rod 50 is disposed and/or loaded with head 72 and/or one or more fasteners connected with vertebrae V. Engagement surface 24 is manually engageable with alar screw 22 such that head 62 mates with the mating element of body 16, as described herein. In some embodiments, manual engagement of selected alar screw 22 includes snap fit and/or pop fit assembly of engagement surface 24 and head 62, as described herein. A surgical driver is connected with setscrew 28 and setscrew 28 is disposed with opening 20 and setscrew 28 is engaged with surface 26 to provisionally fix or permanently fix alar screw 22 with connector 14 and/or in a selected orientation with tissue. A surgical driver is connected with setscrew 56 and rotated to a predetermined force and/or torque limit to cause the frangible portions of setscrew 56 to separate, as described herein. A surgical driver is connected with setscrew 28 and rotated to a predetermined force and/or torque limit to cause the frangible portions of setscrew 28 to separate, as described herein.

In some embodiments, spinal construct 12 is selectively adjustable at the surgical site and/or in situ, for example, during a revision case or repositioning of one or more components of spinal construct 12 and/or a surgical procedure employing spinal construct 12, as described herein. For example, a surgical driver is connected with setscrew 56 and rotated to remove setscrew 56 from opening 54, and a surgical driver is connected with setscrew 28 and rotated to remove setscrew 28 from opening 20. As such, spinal rod 50 is disposed in a removable configuration to facilitate removal of hardware or the repositioning of one or more components of spinal construct 12, for example, the removal of alar screw 22.

Connector 14 is manipulated and/or a surgical instrument is connected to connector 14 to rotate connector 14, for example, in the directions shown by arrows A in FIG. 9, from spinal rod 50. Upon rotation of connector 14, the side loading implant cavity of receiver 48, the reduced profile configuration of receiver 48 and/or the relative angular configuration of body 16 and receiver 48, facilitate removal and/or release of connector 14 from spinal rod 50. Connector 14 remains attached with alar screw 22, and alar screw 22 is adjusted, for example, by removing at least a portion of alar screw 22 from tissue. In some embodiments, alar screw 22 is backed out from ala region A and/or iliac bone, as shown by arrow B in FIG. 12. In some embodiments, alar screw 22 is selectively adjustable in translation, rotation, depth, angular orientation, coating, deformation and/or replacement relative to one or more components of spinal construct 12 and/or tissue.

Upon selective adjustment of one or more components of spinal construct 12, spinal rod 50 is assembled with connector 14 and setscrew 56 is engaged with surface 52 to provisionally fix or permanently fix spinal rod 50 in a capture configuration with receiver 48 and/or in a selected orientation with tissue, as described herein. Setscrew 28 is engaged with surface 26 to provisionally fix or permanently fix alar screw 22 with connector 14 and/or in a selected orientation with tissue. In some embodiments, a second spinal rod (not shown) is attached to a contra-lateral side of vertebrae V, similar to spinal rod 50.

Upon completion of a procedure, as described herein, the surgical instruments, assemblies and non-implanted components of spinal implant system 10 are removed and the incision(s) are closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of rods, plates, connectors and/or bone fasteners for use with a single vertebral level or a plurality of vertebral levels.

In some embodiments, one or more of fasteners may be engaged with tissue in various orientations, such as, for example, series, parallel, offset, staggered and/or alternate vertebral levels. In some embodiments, one or more of fasteners may comprise multi-axial screws, sagittal angulation screws, pedicle screws, mono-axial screws, uni-planar screws, facet screws, fixed axis screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the components and/or surfaces of spinal implant system 10 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A spinal construct comprising:
a first fastener comprising a shaft configured for attachment with sacral and/or pelvic tissue of a body and a head, the head being coupled to the shaft;
a connector including a first portion and a second portion monolithically formed with the first portion, the first portion comprising an engagement surface, the second portion including a receiver defining a transverse cavity, the head being configured to directly engage the engagement surface to facilitate engagement of the first fastener with the connector, the first portion comprising a first bore configured for engagement with a first setscrew, the second portion comprising a second bore configured for engagement with a second setscrew, the bores each having a circular cross-sectional configuration such that the bores each form a complete circle, the first bore defining a first central axis extending at an acute angle relative to a second central axis defined by the second bore, the second portion comprising first and second arms, the second bore extending through the first arm, inner surfaces of the arms defining the transverse cavity, the first arm comprising an outer surface opposite the inner surface of the first arm and a side surface extending from the inner surface of the first arm to the outer surface of the first arm, the side surface extending substantially perpendicular to the inner and outer surfaces of the first arm, the inner surface of the first arm having a first end and an opposite second end defined by an interface between the inner surface of the first arm and the side wall, the inner surface of the first arm extending substantially perpendicular to the second central axis from the first end to the interface, the outer surface of the first arm extending substantially parallel to the inner surface of the first arm, the first portion comprising an outer surface directly adjacent to the outer surface of the first arm, the outer surface of the first portion and the outer surface of the first arm forming an obtuse angle;

a spinal implant configured for disposal in the transverse cavity and engageable with the receiver between a capture configuration and a removable configuration; and a second fastener connected with the spinal implant, the second fastener being a multi-axial fastener.

2. A spinal construct as recited in claim 1, wherein the transverse cavity is disposed perpendicular relative to the second central axis.

3. A spinal construct as recited in claim 1, wherein the second bore is configured for disposal of the second setscrew, the second bore being in communication with the transverse cavity, the second setscrew being engageable with the spinal implant to fix the receiver with the spinal implant in the capture configuration.

4. A spinal construct as recited in claim 1, wherein an outer surface of the second arm is engageable with tissue of an ala of a sacrum and the second fastener is engageable with tissue of an S1 vertebra of the sacrum.

5. A spinal construct as recited in claim 1, wherein the first bore is configured to orient the first fastener for engagement with tissue of an ala of a sacrum and the second fastener is connected with the spinal implant for engagement with tissue of an S1 vertebra of the sacrum.

6. A spinal construct as recited in claim 1, wherein the bores are disposed in a staggered orientation, the second bore being in communication with the transverse cavity.

7. A spinal construct as recited in claim 1, wherein the bores are staggered along a coronal plane of the body, the second bore being in communication with the transverse cavity.

8. A spinal construct as recited in claim 1, wherein the first and second axes are offset and disposed in a relative angular orientation, the second bore being in communication with the transverse cavity.

9. A spinal construct as recited in claim 1, wherein the second bore extends through the first arm without extending through the second arm.

10. A spinal construct as recited in claim 1, wherein an outer surface of the second arm extends parallel to the outer surface of the first arm.

11. A spinal construct as recited in claim 1, wherein the first portion comprises a body, the body comprising opposite top and bottom walls and a side wall extending circumferentially about the first central axis from the top wall to the bottom wall, the first bore extending through the top and bottom walls without extending through the side wall.

12. A spinal construct as recited in claim 1, wherein the second fastener includes a head, the receiver defining a profile sized for alignment with a profile of the head.

13. A spinal construct as recited in claim 1, wherein the head is substantially spherical.

14. A spinal construct as recited in claim 1, wherein the head includes an outer surface defining a mating surface having opposite planar surfaces and an arcuate surface that extends from one of the planar surfaces to another one of the planar surfaces.

15. A spinal construct as recited in claim 14, wherein the mating surface is configured to mate with the engagement surface.

16. A spinal construct as recited in claim 1, wherein the head includes a socket configured for disposal of a surgical tool.

17. A spinal construct as recited in claim 1, wherein the first fastener includes a neck positioned between the shaft and the head, the neck having a maximum diameter that is less than a maximum diameter of the shaft and a maximum diameter of the head.

18. A spinal construct as recited in claim 1, wherein the head is monolithically formed with the shaft.

19. A spinal construct as recited in claim 1, wherein the second arm comprises an outer surface opposite the inner surface of the second arm, the outer surface of the second arm including a first section and a second section, the first section of the outer surface of the second arm extending at an acute angle relative to the outer surface of the first arm, the second section of the outer surface of the second arm extending parallel to the outer surface of the first arm.

20. A spinal construct comprising:

an alar iliac screw comprising a shaft and a head, the head being coupled to the shaft;

a connector including a first portion and a second portion monolithically formed with the first portion, the first portion comprising an engagement surface, the first portion including a first bore, the second portion including a receiver defining a threaded second bore and a transverse cavity in communication with the second bore, the first bore defining a first central axis extending at an acute angle relative to a second central axis defined by the second bore, the bores each having a circular cross-sectional configuration such that the bores each form a complete circle, the head directly engaging the engagement surface to facilitate engagement of the screw with the connector, the second portion comprising first and second arms, the second bore extending through the first arm, inner surfaces of the arms defining the transverse cavity, the first arm comprising an outer surface opposite the inner surface of the first arm, the outer surface of the first arm extending substantially parallel to the inner surface of the first arm, the first arm comprising a side surface extending from the inner surface of the first arm to the outer surface of the first arm, the side surface extending substantially perpendicular to the inner and outer surfaces of the first arm, the inner surface of the first arm having a first end and an opposite second end defined by an interface between the inner surface of the first arm and the side wall, the inner surface of the first arm extending substantially perpendicular to the second central axis from the first end to the interface, the first portion comprising an outer surface directly adjacent to the outer surface of the first arm, the outer surface of the first portion and the outer surface of the first arm forming an obtuse angle;

a spinal rod connected with the receiver between a capture configuration such that the spinal rod is disposable with the transverse cavity and a coupling member is disposed with the bore and engageable with the spinal rod to fix the receiver with the spinal rod and a removable configuration such that the receiver is rotatably removed from the spinal rod; and a multi-axial fastener connected with the spinal rod.

* * * * *